US006878692B2

(12) United States Patent
Noteborn et al.

(10) Patent No.: US 6,878,692 B2
(45) Date of Patent: Apr. 12, 2005

(54) APOPTIN-ASSOCIATING PROTEIN

(75) Inventors: Mathieu Hubertus M. Noteborn, Leiderdorp (NL); Astrid Adriana A. M. Danen-van Oorschot, Berkel en Rodenrijs (NL); Jennifer Leigh Rohn, Amsterdam (NL)

(73) Assignee: Leadd B.V., Leiden (NL)

( * ) Notice: Subject to any disclaimer, the term of this patent is extended or adjusted under 35 U.S.C. 154(b) by 0 days.

(21) Appl. No.: 09/819,308

(22) Filed: Mar. 27, 2001

(65) Prior Publication Data

US 2002/0019040 A1 Feb. 14, 2002

(30) Foreign Application Priority Data

Mar. 27, 2000 (EP) ................................................ 201108

(51) Int. Cl.[7] ........................ A61K 31/70; C07H 21/02; C07H 21/04; C12N 5/00; C12N 15/63
(52) U.S. Cl. ........................ 514/44; 536/23.1; 536/23.5; 435/325; 435/455
(58) Field of Search ............................... 536/231, 23.4, 536/23.5; 514/44

(56) References Cited

FOREIGN PATENT DOCUMENTS

| EP | 0 921 192 A1 | 6/1999 |
|---|---|---|
| EP | 0 924 296 A2 | 6/1999 |

OTHER PUBLICATIONS

Zhuang et al. Cancer Res 55(3):486–489 (Feb. 1995) "Apoptin, a protein derived from chicken anemia virus . . . ".*
Pietersen et al. Gene Therapy 6:882–892 (1999) " Specific tumor–cell killing with adenovirus . . . ".*
Oorschot et al PNAS 94:5843–5847 (May 1997) "Apoptin induces apoptosis . . . ".*
Bellamy, Christopher O.C., et al., "Cell death in health and disease: the biology and regulation of apoptosis," Seminars in Cancer Biology, vol. 6, pp. 3–16 (1995).
Danen–Van Oorschot, A.A.A.M., et al., "Apoptin induces apoptosis in human transformed and malignant cells but not in normal cells." Proc. Nat'l. Acad Sci. USA vol. 94, pp. 5843–5847 (May 1997).
Danen–van Oorschot, et al., A.A.A.M., "BAG–1 inhibits p53–induced but not apoptin–induced apoptosis," Apoptosis, vol. 2, No. 4, pp 395–402 (1997).
Duke, Richard C., et al, "Cell Suicide in Health and Disease," Scientific American, pp 80–87 (Dec. 1996).
McDonnell, Timothy J., et al., "Implications of apoptotic cell death regulation in cancer therapy," Seminars in Cancer Biology, vol. 6, pp. 53–60 (1995).
Noteborn, M.H.M., et al., "A Single Chicken Anemia Virus Protein Induces Apoptosis," Journal of Virology, vol. 68, No. 1, pp. 346–351 (Jan. 1994).
Noteborn, M.H.M., et al., "Characterization of Cloned Chicken Anemia Virus DNA That Contains All Elements for the Infectious Replication Cycle." Journal of Virology, vol. 65, No. 6, pp. 3131–3139 (Jun. 1991).
Noteborn, Mathieu H.M., et al, "Chicken Anemia Virus Induction of Apoptosis by a Single Protein of a Single–Stranded DNA Virus," Seminars in Virology. vol 8, pp 497–504 (1998).
Noteborn, Mathieu H.M., et al., "Simultaneous expression of recombinant baculovirus–encoded chicken anaemia virus (CAV) proteins VP1 and VP2 is required for formation of the CAV–specific neutralizing epitope," Journal of General Virology, vol. 79, pp. 3073–3077 (1998).
Paulovich, Amanda G , et al , "When Checkpoints Fail," Cell, vol. 88, pp 315–321 (Feb. 7, 1997).
Steller Hermann, "Mechanisms and Genes of Cellular Suicide," Science, vol. 267, pp 1445–1449 (Mar. 10, 1995).
Teodoro, Jose G , et al , "Regulation of Apoptosis by Viral Gene Products," Journal of Virology, vol. 71, No 3, pp 1739–1746 (Mar. 1997).
Thompson, Craig B , "Apoptosis in the Pathogenesis and Treatment of Disease," Science, vol. 267, pp 1456–1462 (Mar. 10, 1995).
Partial European Search Report under Rule 46, paragraph 1 of the European Patent Convention.
Strausberg, Robert, "qy85c09.x1 NCI_CGAP_Brn25 Homo sapiens cDNA clone Image:2018800 3', mRNA sequence", Jan. 7, 1999, Accession No. AI360308.

* cited by examiner

Primary Examiner—Joseph Woitach
(74) Attorney, Agent, or Firm—TraskBritt

(57) ABSTRACT

The invention relates to the field of apoptosis. The invention provides novel therapeutic possibilities, for example novel combinatorial therapies or novel therapeutic compounds that can work alone, sequentially to, or jointly with Apoptin, especially in those cases wherein p53 is (partly) non-functional.

5 Claims, No Drawings

APOPTIN-ASSOCIATING PROTEIN

TECHNICAL FIELD

The invention relates generally to the field of biotechnology and medicine, and more particularly relates to methods and associated means for inducing apoptosis in a cell.

BACKGROUND

Apoptosis is an active and programmed physiological process for eliminating superfluous, altered or malignant cells (Earnshaw, 1995, Duke et al., 1996). Apoptosis is characterized by shrinkage of cells, segmentation of the nucleus, condensation and cleavage of DNA into domain-sized fragments, and is then generally followed by internucleosomal degradation. The apoptotic cells fragment into membrane-enclosed apoptotic bodies. Finally, neighboring cells and/or macrophages will rapidly phagocytose these dying cells (Wyllie et al., 1980, White, 1996).

Cells grown under tissue-culture conditions and cells from tissue material can be analyzed for being apoptotic with agents staining DNA, as e.g. DAPI, which stains normal DNA strongly and regularly, whereas apoptotic DNA is stained weakly and/or irregularly (Noteborn et al., 1994, Telford et al., 1992).

The apoptotic process can be initiated by a variety of regulatory stimuli (Wyllie, 1995, White 1996, Levine, 1997). Changes in the cell survival rate play an important role in human pathogenesis of diseases, e.g. in cancer development and auto-immune diseases, where enhanced proliferation or decreased cell death (Kerr et al., 1994, Paulovich, 1997) is observed. A variety of chemotherapeutic compounds and radiation have been demonstrated to induce apoptosis in tumor cells, in many instances via wild-type p53 protein (Thompson, 1995, Bellamy et al., 1995, Steller, 1995, McDonell et al., 1995).

Many tumors, however, acquire a mutation in p53 during their development, often correlating with poor response to cancer therapy. Certain transforming genes of tumorigenic DNA viruses can inactivate p53 by directly binding to it (Teodoro, 1997). An example of such an agent is the large T antigen of the tumor DNA virus SV40. For several (leukemic) tumors, a high expression level of the proto-oncogene Bcl-2 or Bcr-abl is associated with a strong resistance to various apoptosis-inducing chemotherapeutic agents (Hockenberry 1994, Sachs and Lotem, 1997). For such tumors lacking functional p53 (representing more than half of the tumors) alternative anti-tumor therapies are under development based on induction of apoptosis independent of p53 (Thompson 1995, Paulovich et al., 1997). One has to search for the factors involved in induction of apoptosis, which do not need p53 and/or cannot be blocked by anti-apoptotic activities, such as Bcl-2 or Bcr-abl-like ones. These factors might be part of a distinct apoptosis pathway or might be (far) downstream of the apoptosis inhibiting compounds.

Apoptin is a small protein derived from chicken anemia virus (CAV; Noteborn and De Boer, 1995, Noteborn et al., 1991, Noteborn et al., 1994; 1998a), which can induce apoptosis in human malignant and transformed cell lines, but not in untransformed human cell cultures. In vitro, Apoptin fails to induce programmed cell death in normal lymphoid, dermal, epidermal, endothelial and smooth-muscle cells. However, when normal cells are transformed they become susceptible to apoptosis by Apoptin. Long-term expression of Apoptin in normal human fibroblasts revealed that Apoptin has no toxic or transforming activity in these cells (Danen-van Oorschot, 1997; Noteborn, 1996). In normal cells, Apoptin is found predominantly in the cytoplasm, whereas in transformed or malignant cells i.e. characterized by hyperplasia, metaplasia or dysplasia, it is located in the nucleus, suggesting that the localization of Apoptin is related to its activity (Danen-van Oorschot et al. 1997).

Apoptin-induced apoptosis occurs in the absence of functional p53 (Zhuang et al., 1995a), and cannot be blocked by Bcl-2, Bcr-abl (Zhuang et al., 1995), or the Bcl-2-associating protein BAG-1 (Danen-Van Oorschot, 1997a, Noteborn, 1996). Therefore, Apoptin is a therapeutic compound for the selective destruction of tumor cells, or other hyperplasia, metaplasia or dysplasia, especially for those tumor cells which have become resistant to (chemo)-therapeutic induction of apoptosis, due to the lack of functional p53 and (over)-expression of Bcl-2 and other apoptosis-inhibiting agents (Noteborn and Pietersen, 1998). It appears, that even pre-malignant, minimally transformed cells, are sensitive to the death-inducing effect of Apoptin. In addition, Noteborn and Zhang (1998) have shown that Apoptin-induced apoptosis can be used as diagnosis of cancer-prone cells and treatment of cancer-prone cells.

The fact that Apoptin does not induce apoptosis in normal human cells, at least not in vitro, shows that a toxic effect of Apoptin treatment in vivo will be very low. Noteborn and Pietersen (1998) and Pietersen et al. (1999) have provided evidence that adenovirus expressed Apoptin does not have an acute toxic effect in vivo. In addition, in nude mice it was shown that Apoptin has a strong anti-tumor activity.

However, to further enlarge the array of therapeutic anti-cancer or anti-auto-immune-disease compounds available in the art, additional therapeutic compounds are desired that are designed to work alone, sequentially to, or jointly with Apoptin, especially in those cases wherein p53 is (partly) non-functional.

SUMMARY OF THE INVENTION

The invention provides novel therapeutic possibilities, for example novel combinatorial therapies or novel therapeutic compounds that can work alone, sequentially to, or jointly with Apoptin, especially in those cases wherein p53 is (partly) non-functional.

In a first embodiment, the invention provides an isolated or recombinant nucleic acid or functional equivalent or fragment thereof encoding an Apoptin-associating proteinaceous substance capable of providing apoptosis, alone or in combination with other apoptosis inducing substances, such as Apoptin. Proteinaceous substance herein is defined as a substance comprising a peptide, polypeptide or protein, optionally having been modified by for example glycosylation, myristilation, phosphorylation, the addition of lipids, by homologous or heterologous di- or multi-merization, or any other (post-translational) modifications known in the art.

Apoptin-associating herein is defined as belonging to the cascade of substances specifically involved in the cascade of events found in the apoptosis pathway as inducible by Apoptin, preferably those substances that are specifically involved in the p53-independent apoptosis pathway.

In a preferred embodiment, the invention provides an isolated or recombinant nucleic acid or functional equivalent or fragment thereof encoding an Apoptin-associating proteinaceous substance capable of providing apoptosis derived from a cDNA library, preferably a vertebrate cDNA library, such as derivable from poultry, but more preferably a mammalian cDNA library, preferably wherein the cDNA library comprises human cDNA. An Apoptin-associating proteinaceous substance obtained by determining a vertebrate homologue (preferably human) of an Apoptin-associating proteinaceous substance derived from an invertebrate cDNA library is also included.

In another embodiment, the invention provides an isolated or recombinant nucleic acid or functional equivalent or fragment thereof encoding an Apoptin-associating proteinaceous substance capable of providing apoptosis. It is capable of hybridizing to a nucleic acid molecule encoding an Apoptin-associating proteinaceous substance capable of providing apoptosis as shown in SEQ ID NO 1 and/or SEQ ID NO 9, in particular encoding a novel protein capable of providing apoptosis or functional equivalent or functional fragment thereof called Apoptin-associating protein 5, abbreviated herein also as AAP-5. SEQ ID NO 1 shows a fragment of the complete AAP-5 fragment as depicted in SEQ ID NO 9. Both nucleotide sequences encode a protein (SEQ ID NO 2 and SEQ ID NO 10) with at least the capability of binding to Apoptin and providing apoptosis (as disclosed herein within the experimental part). Of course, an isolated or recombinant nucleic acid or functional equivalent or fragment thereof encoding an additional Apoptin-associating proteinaceous substance capable of associating with the partial or full-length AAP-5 protein is herewith also provided. The means and methods to arrive at such an additional protein located in the Apoptin cascade follow those of the detailed description given herein. Knowledge derived from studying the partial or full-length AAP-5 is exploited to determine a functional pathway in which partial or full-length AAP-5 is involved, thus allowing the design of further therapeutic means of intervening in such a pathway.

In particular, the invention provides an isolated or recombinant nucleic acid or functional equivalent or fragment thereof encoding an Apoptin-associating proteinaceous substance capable of providing apoptosis being at least 60% homologous, preferably at least 70%, more preferably at least 80%, even more preferably at least 90% and most preferably at least 95% homologous to a nucleic acid molecule, or to a functional equivalent or functional fragment thereof, encoding an Apoptin-associating proteinaceous substance as shown in SEQ ID NO 1 or SEQ ID NO 9.

Furthermore, the invention provides a vector comprising a nucleic acid according to the invention. Examples of such a vector are given in the detailed description given herein; such as vector pMT2SM-AAP-5, pMT2SM vector expressing Myc-tagged AAP-5 cDNA, a plasmid expressing an Apoptin-associating protein fragment, and so on. This and other vectors are for example, useful in finding additional Apoptin-associating proteinaceous substances from the cascade, as defined above.

In yet another embodiment, the invention provides a vector comprising a nucleic acid according to the invention, the vector comprising a gene-delivery vehicle, making the invention very useful in gene therapy. By equipping a gene delivery vehicle with a nucleic acid according to the invention, and by targeting the vehicle to a cell or cells that have been over-proliferating and/or have shown decreased death rates, the gene delivery vehicle provides the cell or cells with the necessary means for apoptosis, providing far reaching therapeutic possibilities.

Furthermore, the invention provides a host cell comprising a nucleic acid or a vector according to the invention. Examples comprise transduced bacterial or yeast cells as described in the detailed description herein. Preferred is a host cell according to the invention which is a transduced eukaryotic cell, such as a yeast cell or a vertebrate cell, such as mammalian or Cos cells transduced with a nucleic acid or vector according to the invention. The cells are in general capable to express or produce a proteinaceous substance capable of providing apoptosis with the ability to associate with Apoptin.

The invention furthermore provides an isolated or recombinant Apoptin-associating proteinaceous substance capable of providing apoptosis. As for example shown herein in SEQ ID NO 2 and SEQ ID NO 10, expression of such Apoptin-associating proteinaceous substance in cells, such as tumor cells, or other over-proliferating cells, induces the apoptotic process. It can do so alone, or in the presence of other apoptosis inducing substances such as Apoptin, and especially so independent of p53, showing that also in those cases where (functional) p53 is absent apoptosis can be induced by a substance according to the invention. In particular, the invention provides a proteinaceous substance according to the invention encoded by a nucleic acid according to the invention, for example comprising at least a part of an amino acid sequence as shown in SEQ ID NO 2 or SEQ ID NO 10 (AAP-5) or a functional equivalent or functional fragment thereof capable of providing apoptosis alone or in combination with other apoptosis inducing substances such as Apoptin.

The invention also provides an isolated or synthetic antibody specifically recognizing a proteinaceous substance or functional equivalent or functional fragment thereof according to the invention. Such an antibody is, for example, obtainable by immunizing an experimental animal with an Apoptin-associating proteinaceous substance or an immunogenic fragment or equivalent thereof. Then the polyclonal antibodies are harvested from the immunized animal, or obtainable by other methods known in the art, such as by producing monoclonal antibodies, or (single chain) antibodies or binding proteins expressed from recombinant nucleic acid derived from a nucleic acid library, for example obtainable via phage display techniques. Examples of such an antibody are given in the detailed description herein.

With such an antibody, the invention also provides a proteinaceous substance specifically recognizable by such an antibody according to the invention, for example, obtainable via immunoprecipitation, Western Blotting, or other immunological techniques known in the art. Furthermore, the invention provides use of a nucleic acid, vector, host cell, or proteinaceous substance according to the invention for the induction of tumor-specific apoptosis, as for example shown in Table 1. In particular, such use is provided wherein the apoptosis is p53-independent. In particular, such use is also provided further comprising use of a nucleic acid encoding Apoptin or a functional equivalent or fragment thereof or use of Apoptin or a functional equivalent or fragment thereof. As can be seen from Table 1, combining these Apoptin-inducing substances increases the percentage apoptosis of treated tumor cells.

Such use as provided by the invention is particularly useful from a therapeutic viewpoint. The invention provides herewith, a pharmaceutical composition comprising a nucleic acid, vector, host cell, or proteinaceous substance according to the invention. In addition, such a pharmaceutical composition according to the invention is provided further comprising a nucleic acid encoding Apoptin or a functional equivalent or fragment thereof.

Such a pharmaceutical composition is in particular provided for the induction of apoptosis, for example wherein the apoptosis is p53-independent, for the treatment of a disease where enhanced cell proliferation or decreased cell death is observed, as is in general the case when the disease comprises cancer or auto-immune disease. Herewith, the invention provides a method for treating an individual carrying a disease where enhanced cell proliferation or decreased cell death is observed comprising treating the individual with a pharmaceutical composition according to the invention. In particular, these compositions comprise a factor of an apoptosis pathway, which is specific for transformed cells. Therefore, these compositions are essential for new treatments, but also for diagnosis of diseases related with aberrances in the apoptotic process, such as cancer, cancer-proneness and auto-immune diseases.

The invention will be explained in more detail in the following detailed description, which is not limiting the invention.

DETAILED DESCRIPTION OF THE INVENTION

The yeast-2 hybrid system (Durfee et al., 1993) was used to identify Apoptin-associating cellular compounds, which are essential in the induction of apoptosis. The used system is an in vivo strategy to identify human proteins capable of physically associating with Apoptin. It has been used to screen cDNA libraries for clones encoding proteins capable of binding to a protein of interest (Fields and Song, 1989, Yang et al., 1992). The invention provides for example a novel Apoptin-associating protein, which is named Apoptin-associating protein 5 abbreviated as AAP-5. The invention also provides a method for inducing apoptosis through interference with the function of this newly discovered AAP-5 protein or functional equivalents or fragments thereof and/or the induction of apoptosis by means of (over)expression of AAP-5 or related gene or functional equivalents or fragments thereof.

The invention also provides an anti-tumor therapy based on the interference with the function of AAP-5-like proteins and/or its (over)expression. The presence of AAP-5-like protein can result in the induction of the opposite process of cell transformation, namely apoptosis. The invention furthermore provides the mediator of Apoptin-induced apoptosis. The invention provides a therapy for cancer, autoimmune diseases or related diseases which is based on AAP-5-like proteins alone or in combination with Apoptin and/or Apoptin-like compounds.

Construction of pGBT9-VP3

For the construction of the bait plasmid, which enables the identification of Apoptin-associating proteins by means of a yeast-two-hybrid system, plasmid pET-16b-VP3 (Noteborn, unpublished results) was treated with NdeI and BamHI. The 0.4 kb NdeI-BamHI DNA fragment was isolated from low-melting-point agarose. Plasmid pGBT9 (Clontech Laboratories, Inc, Palo Alto, USA) was treated with the restriction enzymes EcoRI and BamHI. The approximate 5.4-kb DNA fragment was isolated and ligated to an EcoRI-NdeI linker and the 0.4-kb DNA fragment containing the Apoptin-encoding sequences starting from its own ATG-initiation codon. The final construct containing a fusion gene of the GAL4-binding domain sequence and Apoptin under the regulation of the yeast promoter ADH was called pGBT-VP3 and was proven to be correct by restriction-enzyme analysis and DNA-sequencing according to the Sanger method (1977). All cloning steps were essentially carried out as described by Maniatis et al. (1992). The plasmid pGBT-VP3 was purified by centrifugation in a CsCl gradient and column chromatography in Sephacryl S500 (Pharmacia).

GAL4-activation Domain-tagged cDNA Library

The expression vector pACT, containing the cDNAs from Epstein-Barr-virus-transformed human B cells fused to the GAL4 transcriptional activation domain, was used for detecting Apoptin-associating proteins. The pACT cDNA library is derived from the lambda-ACT cDNA library, as described by Durfee et al. 1993.

Bacterial and Yeast Strains

The E. coli strain JM109 was the transformation recipient for the plasmid pGBT9 and pGBT-VP3. The bacterial strain electromax/DH10B was used for the transformation needed for the recovery of the Apoptin-associating pACT-cDNAs, and was obtained from GIBCO-BRL, USA. The yeast strain Y190 was used for screening the cDNA library, and all other transformations, which are part of the used yeast-two-hybrid system.

Media

For drug selections Luria Broth (LB) plates for E. coli were supplemented with ampicillin (50 microgram per ml). Yeast YPD and SC media were prepared as described by Rose et al. (1990). Transformation of competent yeast strain Y190 with plasmids pGBT-VP3 and pACT-cDNA and screening for beta-galactosidase activity was performed.

The yeast strain Y190 was made competent and transformed according to the methods described by Klebe et al. (1983). The yeast cells were first transformed with pGBT-VP3 and subsequently transformed with pACT-cDNA, and these transformed yeast cells were grown on histidine-minus plates, also lacking leucine and tryptophan.

Hybond-N filters were laid on yeast colonies, which were histidine-positive and allowed to wet completely. The filters were lifted and submerged in liquid nitrogen to permeabilize the yeast cells. The filters were thawed and laid with the colony side up on Whattman 3MM paper in a petri dish with Z-buffer (Per liter: 16.1 gr $Na_2HPO_4.7H_2O$, 5.5 gr $NaH_2PO_4.H_2O$, 0.75 gr KCl and 0.246 gr $MgSO_4.7H_2O$, pH 7.0) containing 0.27% beta-mercapto-ethanol and 1 mg/ml X-gal. The filters were incubated from at least 15 minutes to overnight.

Recovery of Plasmids from Yeast

Total DNA from yeast cells, which were histidine- and beta-galactosidase-positive, were prepared by using the glusulase-alkaline lysis method as described by Hoffman and Winston (1987) and used to transform Electromax/DH10B bacteria via electroporation using a Bio-Rad GenePulser according the manufacturer's specifications. Transformants were plated on LB media containing the antibiotic agent ampicillin.

Isolation of Apoptin-associating pACT Clones

By means of colony-filter assay, the colonies were lysed and hybridized to a radioactive-labeled 17-mer oligomer, which is specific for pACT (see also section Sequence analysis). Plasmid DNA was isolated from the pACT-clones, and by means of xhoI digestion, it was analyzed for the presence of a cDNA insert.

Sequence Analysis

The subclone containing the sequence encoding Apoptin-associating protein was partially sequenced using dideoxy NTPs according to the Sanger-method, which was performed by Eurogentec, Seraing, Belgium or BaseClear, Leiden, The Netherlands). The used sequencing primer was a pACT-specific 17-mer comprising of the DNA-sequence 5'-TACCACTACAATGGATG-3' (SEQ ID NO 3) or internal primers comprising the described novel AAP-5 sequences. The sequences of the Apoptin-associating cDNAs were compared with known gene sequences from the EMBL/Genbank.

Generation and Testing of Antibodies

In order to generate polyclonal antisera against the protein predicted to be encoded by the partial AAP-5 clone, Eurogentec (Belgium) designed three peptides predicted to be antigenic. These peptides were, for AAP-5:1) Residues 27–41: CGGATHVYRYHRGESK (SEQ ID NO 4); 2) Residues 49–63: GNGQRKDRKKTSLGPC (SEQ ID NO 5); and 3) Residues 71–85: EHAPEASQPAENISKC (SEQ ID NO 6). (Note: numbering same as in SEQ ID NO 2, and underlined C residues are added for technical reasons and are not part of the actual AAP sequence). These peptides were synthesized at Eurogentec and all subsequent antibody syntheses were also performed there.

Briefly, the three peptides were coupled to KLH and injected as a cocktail into two separate specific pathogen free rabbits with an immunization schedule of one injection and three subsequent boosts. Blood samples were taken both before and after immunization. The sera were tested in-house by ELISA for specific reactivity to the peptide cocktail. The titers from each rabbit were high. Furthermore, for certain subsequent purposes, the AAP-5 antibodies were immune-purified using peptide cocktail coupled to immobilized diaminodipropylamine agarose columns (Pierce) according to the manufacturer's protocol.

The AAP-5 antibody of the two generated with the highest affinity was selected for further use. We tested the efficacy of this antibody by transfecting 6 cm plates of sub-confluent primate COS-7 and human U2OS cells using the calcium phosphate co-precipitation method with 5 mg of the AAP-5-myc construct (partial clone), and as a control, untransfected cells. Post-transfection, cells were washed briefly in PBS, lysed in RIPA buffer (10 mM Tris 7.5, 150 mM NaCl, 0.1% SDS, 1.0% NP-49 and 1.0% sodium deoxycholate), clarified by centrifugation, and the supernatant fractionated on SDS-denaturing polyacrylamide gel electrophoresis. Proteins were Western-transferred to PVDF membranes (Immobilon, Millipore) using standard methodology. Membranes were blocked in 5% non-fat dry milk in Tris-buffered saline containing 0.1% Tween-20, then incubated in the unpurified AAP-5 antisera at a concentration of 1:5,000. After a brief wash, membranes were further incubated in HRP-conjugated goat-anti-rabbit Ig at a concentration of 1:2,000. After a thorough series of wash steps, proteins were detected using enhanced chemiluminescence (Amersham) according to the manufacturer's protocol, and exposed to x-ray film and developed using standard automated machinery. In addition, we tested the purified AAP-5 antibody using immunoprecipitation in a manner the same as above, except that after centrifugation, the supernatant was added to 10 ml of purified AAP-5 antibody pre-coupled to protein-A-sepharose beads, incubated for 1 hour with tumbling, then washed before fractionation of SDS-PAGE gels and Western analysis. Detection in this case was performed with the anti-myc tag monoclonal antibody 9E10 (Evan et al.). Finally, the purified AAP-5 antibody was tested for utility in immunofluorescence by including glass coverslips in the above transfections. Coverslips were fixed with 4% paraformaldehyde, blocked with normal goat serum, incubated in a concentration of 1:10, washed, incubated in a 1:100 dilution of conjugated goat-anti-rabbit Ig, mounted in DAPI/DABCO/glycerol and visualized with fluorescence microscopy.

Northern Analysis

To examine the RNA expression pattern of AAP-5, we tested commercially-manufactured Northern blots (Invitrogen, cat. 1999, #D2801-50) containing poly-A+ RNA from human fetal brain, liver, lung, muscle tissue and from adult lung. The DNA probe was derived from an XhoI restriction fragment encompassing the entire insert of the AAP-5-myc partial clone. This probe was labeled with $^{32}$P-dATP using the MegaPrime kit of Amersham. All prehybridization, hybridization and washing steps were done according to the Northern blot manufacturer's recommendation. Blots were subjected to autoradiography and developed using standard automated methods.

Cloning of Full-length AAP-5

The complete ORF of AAP-5 was amplified from a human brain cDNA library (Clontech—Marathon Ready cDNA). The RT-PCR was performed according to the manufacturer's instructions (Clontech—Advantage®2 PCR kit).

| RT-PCR | Sample volume 50 µl |
| --- | --- |
| Brain cDNA | 2 µl |
| 5'-primer (50 µM) | 1 µl |
| 3'-primer (50 µM) | 1 µl |
| 10x cDNA PCR reaction buffer | 5 µl |
| dNTP mix (10 mM) | 1 µl |
| 50x Advantage 2 Polymerase mix | 1 µl |
| Sterile water | 39 µl |

The cycling program for the RT-PCR in a Perkin-Elmer 9600 thermocycler was performed as follows:

| | | |
| --- | --- | --- |
| 94° C. | 30 sec | 1 cycle |
| 94° C. | 5 sec | 30 cycles |
| 68° C. | 3 min | |

The sequences for the RT-PCR primers were generated from AAP-5 genomic sequence identified on chromosome 11. These include:

```
AAP-5 - 5'primer
5'-GGA GCC ATG GAC AAC TGT TTG GCG GCC G-3'
(SEQ ID NO 7)

AAP-5 - 3'primer
5'-GTG ATG GCA GTG ATG GTC AAC ATC ACA C-3'
(SEQ ID NO 8)
```

The PCR products were cloned into the pCR®4-TOPO vector according to the instructions of the TOPO-TA cloning® kit from Invitrogen. The sequences of the PCR products were generated with the Applied Biosystem (ABI) Prism®BigDye™Terminator sequencing kit and analyzed on a ABI 310 capillary sequencer.

The sequencing primers were the PCR primers (5' and 3') and the following:

```
AAP-5 - #5F
5'-ATA TTA TTC ATC TGT GCC AGA GG-3' (sense)
(SEQ ID NO 11)

AAP-5 - #5R
5'-CCT CTG GCA CAG ATG AAT AAT AT-3' (antisense)
(SEQ ID NO 12)
```

Biochemical Interactions of AAP-5

Interactions were determined by co-transfection followed by standard co-immunoprecipitation analysis exactly as described in the results section under "Co-immunoprecipitation of Myc-tagged AAP-5 protein with Apoptin in a transformed mammalian cell system". In this case, the amount of DNA in the two-way co-transfection was 10 mg, and the partial clones were used (except AAP-3, of which a full-length sequence was used). Pull-downs were performed by IP'ing with the appropriate AAP antibody and performing Western blot analysis with the anti-myc tag 9E10. Polyclonal antibodies directed against AAP-5, AAP-4 and AAP-3 were used.

Antibodies against AAP-3 and AAP-4 were obtained as described in the section "Generation and testing of antibodies". Peptides used for raising antibodies against AAP-3: 1) IYQRSGERPVTAGEE (SEQ ID NO 13), 2) DEQVPDSI-DAREIFD (SEQ ID NO 14) and 3) RSINDPEHPLTLEEL (SEQ ID NO 15). Peptides used to raise antibodies against AAP-4: 1) EESTPVHDSPGKDDA (SEQ ID NO 16), 2) DSFKTKDSFRTAKSK (SEQ ID NO 17) and 3) IDIDISS-RRREDQSL (SEQ ID NO 18).

AAP-5 Full-length: Appearance and Effects on Tumor Cells

In order to characterize the full-length AAP-5 protein, we expressed constructs encoding the full-length clones in cells and analyzed them by immunofluorescence staining. AAP-5 was analyzed as described in the results section under "Over-expression of the novel AAP-5 protein in human transformed cells induces the apoptotic process", using Saos-2 and U2OS tumor cells. AAP-5 was stained with 9E10 to detect the fused myc tag. As comparison controls, Apoptin was expressed alone and in combination with AAP-5, and a construct expressing LacZ was included as a negative control. For these experiments, we examined cells after 2 and 5 days of transfection.

Results

Apoptin specifically induces apoptosis in transformed cells, such as cell lines derived from human tumors. To identify the essential compounds in this cell-transformation-specific and/or tumor-specific apoptosis pathway, a yeast genetic screen was carried out. We have used a human cDNA library, which is based on the plasmid vector pACT containing the complete cDNA copies made from Epstein-Barr virus-transformed human B cells (Durfee et al., 1993).

Construction of a Bait Plasmid Expressing a Fusion Gene Product of GAL4-DNA-binding Domain and Apoptin To examine the existence of Apoptin-associating proteins in the human transformed/tumorigenic cDNA library, a so-called bait plasmid had to be constructed. To that end, the complete Apoptin-encoding region, flanked by about 40 base pairs downstream from the Apoptin gene, was cloned in the multiple cloning site of plasmid pGBT9. The final construct, called pGBT-VP3, was analyzed by restriction-enzyme analysis and sequencing of the fusion area between Apoptin and the GAL4-DNA-binding domain.

A gene(fragment) encoding an Apoptin-associating protein is determined by transactivation of a GAL4-responsive promoter in yeast. The Apoptin gene is fused to the GAL4-DNA-binding domain of plasmid pGBT-VP3, whereas all cDNAs derived from the transformed human B cells are fused to the GAL4-activation domain of plasmid pACT. If one of the proteinaceous substances encoded by the cDNAs binds to Apoptin, the GAL4-DNA-binding domain will be in the vicinity of the GAL4-activation domain resulting in the activation of the GAL4-responsive promoter, which regulates the reporter genes HIS3 and LacZ.

The yeast clones containing plasmid expressing Apoptin and a plasmid expressing an Apoptin-associating protein fragment can grow on a histidine-minus medium and will stain blue in a beta-galactosidase assay. Subsequently, the plasmid with the cDNA insert encoding the Apoptin-associating protein can be isolated and characterized. Before we could do so, however, we have determined that transformation of yeast cells with pGBT-VP3 plasmid alone, or in combination with an empty pACT vector, did not result in the activation of the GAL4-responsive promoter. Identification of Apoptin-associating protein encoded by cDNA derived from a human transformed B cell line.

One yeast colony was found, which upon transformation with pGBT-VP3 and pACT-cDNA, was able to grow on a histidine-minus medium (also lacking leucine and tryptophan) and stained blue in a beta-galactosidase assay. These results indicate that the observed yeast colony contains besides the bait plasmid pGBT-VP3, a pACT plasmid encoding a potential Apoptin-associating protein. Plasmid DNA was isolated from the positive yeast colony, which was transformed in bacteria. By means of a filter-hybridization assay using a pACT-specific labeled DNA-probe, the clone containing pACT plasmid could be determined. Subsequently, pACT DNA was isolated and digested with restriction enzyme XhoI, which resulted in the presence of an approximately 1.0-kbp cDNA insert. Finally, the cDNA insert of the pACT plasmid containing the cDNA insert was sequenced by using the Sanger method (Sanger et al., 1977).

Description of Apoptin-associating Proteins

The yeast genetic screen for Apoptin-associating proteins resulted in the detection of a cDNA clone comprising a single type of protein, namely a novel protein called Apoptin-associating protein 5, abbreviated as AAP-5.

The determined DNA sequence part of the AAP-5 cDNA clone is shown below in SEQ ID NO 1. SEQ ID NO 1 shows the partial sequence of vector pMT2SM-AAP-5.

| | | | | |
|---|---|---|---|---|
| CCAATGGCTG | AATTCATGGA | CTATACTTCA | AGTCAGTGTG | GGAAATATTA |
| TTCATCTGTG | CCAGAGGAAG | GAGGGGCAAC | CCATGTCTAT | CGTTATCACA |
| GAGGCGAGTC | GAAGCTGCAG | ATGTGCTTGG | ACATAGGGAA | TGGTCAGAGA |
| AAAGACAGAA | AAAAGACATC | CCTTGGTCCT | GGAGGCAGCT | ATCAAATATC |
| AGAGCATGCT | CCAGAGGCAT | CCCAGCCTGC | TGAGAACATC | TCTAAGGACC |
| TCTACATAGA | AGTATATCCA | GGGACCTATT | CTGTCACTGT | GGGCTCAAAT |
| GACTTAACCA | AGAAGACTCA | TGTGGTAGCA | GTTGATTCTG | GACAAAGCGT |
| GGACCTGGTC | TTCCCTGTGT | GATGTTGACC | ATCACTGCCA | TCACATCACC |
| TTTTTTTAAG | TAGTAAGAAT | AAAGCCACTG | TATGATTCTC | TTAATAGCTA |
| TACATTAATC | CTGTTTTTAG | TGCTGACTGG | GTCAGCCTTC | CGGGAACTGG |
| AGTCTGTCTC | TTTCAGTGCT | TTTTTGTTTG | TTTGGTTGGT | TGTTTTTTGA |
| GACAGTCTCG | CTCTGTTGCC | CAGGCTGGAG | TGCAGTGGCG | TGATCTCGGC |
| TCACCGCAAG | TTCCGCCTCC | CGGGTTCACA | CCATTCTCCT | GCCTCAGCCT |
| CCCGAGTAGC | TGGCACTACA | GGCACCCGCC | ACCATGCCCG | GCTATTTTTT |
| TTGTATTTTT | AGTAGAGACG | GGGTTTCACC | ATGTTGGCCA | GGATGGTCTC |

```
                       -continued
GATCTCTTGA   CCTCGTGATC   CACCCACCTT   GGCCTCCCAA   AGTGTTGGGA
TTACAGGCGT   GAGCCACCGC   GCCCGGCCTC   AGTGCCTTTT   TTAACTTGAG
GGTGTAGAGG   TCCTCCACGC   TTGTTTGCCT   GAAAGTAATA   TAATGATGCT
GTCTGAACAG   GTTTTACTGC   TTGCTTTCCA   AGTAAAGGTT   AATTATGATA
ATAAAGAGAT   TTGGGCCTTC   GTGGCCTCGA   G (SEQ ID NO 1)
```

The amino acid sequence, derived from the detected DNA sequence of clone AAP-5 is given in SEQ ID NO 2. HEGPMAEFMDYTSSQCGKYYSSVPEEG-GATHVYRYHRGESKLHMCLDIGNGQRKDRK KTSLGPGGSYQISEHAPEASQPAENI-SKDLYIEVYPGTYSVTVGSNDLTKKTH VVAVDSGQS-VDLVFPV (SEQ ID NO. 2).

SEQ ID NO 2 shows the amino-acid sequence of the analyzed region of the Apoptin-associating clone AAP-5. In addition, the three C-terminal amino acids H-E-G (bold) of the multiple cloning site of pACT are given above in SEQ ID NOS 3–5 to illustrate that the AAP-5 amino acid sequence is in frame with the GAL4-activation domain. This feature proves that the AAP-5 region is indeed synthesized in yeast cells.

Construction of an expression vector for the identification of AAP-5 protein in mammalian cells was also tested.

To study whether the cloned cDNA AAP-5 indeed encode (Apoptin-associating) a protein product, the following experiments were carried out. The DNA plasmid pMT2SM contains the adenovirus 5 major late promoter (MLP) and the SV40 ori enabling high levels of expression of foreign genes in transformed mammalian cells, such as SV-40-transformed Cos cells. Furthermore, the pMT2SM vector contains a Myc-tag (amino acids: EQKLISEEDL (SEQ ID NO 19)) which is in frame with the foreign-gene product. This Myc-tag enables the recognition of e.g. Apoptin-associating proteins by means of the Myc-tag-specific 9E10 antibody.

The pMT2SM vector expressing Myc-tagged AAP-5 cDNA was constructed as follows. The pACT-AAP-5 cDNA clone was digested with the restriction enzyme XhoI and the cDNA insert was isolated. The expression vector pMT2SM was digested with XhoI and treated with calf intestine alkaline phosphatase and ligated to the isolated AAP-5 cDNA inserts. By sequence analysis, the pMT2SM constructs containing the AAP-5 cDNA in the correct orientation were identified.

The synthesis of Myc-tagged AAP-5 protein was analyzed by transfection of Cos cells with plasmid pMT2SM-AAP-5. As negative control, Cos cells were mock-transfected. Two days after transfection, the cells were lysed and Western-blot analysis was carried out using the Myc-tag-specific antibody 9E10. The Cos cells transfected with pMT2SM-AAP-5 were proven to synthesize a specific Myc-tagged AAP-5 product with the size of approximately 18 kDa. As expected, the lysates of the mock-transfected Cos cells did not contain a protein product reacting with the Myc-tag-specific antibodies. These results indicate that we have been able to isolate a cDNA that is able to produce a protein product with the ability to associate to the apoptosis-inducing protein Apoptin.

Co-immunoprecipitation of Myc-tagged AAP-5 protein with Apoptin in a transformed mammalian cell system.

Next, the association of Apoptin and the AAP-5 protein was analyzed by means of co-immunoprecipitations using the Myc-tag-specific antibody 9E10. The 9E10 antibodies were shown not to bind directly to Apoptin, which enables the use of 9E10 for carrying out co-immunoprecipitations with (myc-tagged) Apoptin-associating proteins and Apoptin. To that end, Cos cells were co-transfected with plasmid pCMV-VP3 encoding Apoptin and with plasmid pMT2SM-AAP-5. As a negative control, cells were transfected with pCMV-VP3 expressing Apoptin and a plasmid pcDNA3.1.LacZ-myc/His-LacZ encoding the myc-tagged beta-galactosidase, which does not associate with Apoptin.

Two days after transfection, the cells were lysed in a buffer consisting of 50 mM Tris (7.5), 250 mM NaCl, 5 mM EDTA, 0.1% Triton X100, 1 mg/ml $Na_4P_2O_7$ and freshly added protease inhibitors such as PMSF, Trypsine-inhibitor, Leupeptine and $Na_3VO_4$. The specific proteins were immuno-precipitated as described by Noteborn et al. (1998) using the Myc-tag-specific antibodies 9E10, and analyzed by Western blotting.

Staining of the Western blot with 9E10 antibodies and 111.3 antibodies, which are specifically directed against myc-tag and Apoptin, respectively, showed that the "total" cell lysates contained the 16-kDa Apoptin product and the Myc-tagged AAP-5 protein of 18 kDa. By means of a specific LacZ polyclonal antibody also the beta-galactosidase product could be visualized.

Immunoprecipitation of the Myc-tagged AAP-5 products was accompanied by the immunoprecipitation of Apoptin product of 16 kDa. In contrast, immunoprecipitation of myc-tagged beta-galactosidase did not result in a detectable co-precipitation of the Apoptin protein. In addition, immunoprecipitation of the Apoptin protein, by means of a polyclonal antibody directed against the C-terminal part of Apoptin (Noteborn and Danen, unpublished results), was accompanied by the immunoprecipitation of the AAP-5 product of 18 kDa, but not by beta-galactosidase protein.

In total, three independent immunoprecipitation experiments were carried out, which all showed the specific associating ability of Apoptin protein to the AAP-5 protein. These results indicate that the novel determined AAP-5 protein is able to specifically associate with Apoptin not only in the yeast background, but also in a mammalian transformed cellular system. Over-expression of the novel AAP-5 protein in human transformed cells induces the apoptotic process.

In addition, we have examined whether AAP-5 carries apoptotic activity. First, we have analyzed the cellular localization of the novel AAP-5 protein in human transformed cells. To that end, the human osteosarcoma-derived Saos-2 cells and U2OS cells were transfected, as described by Danen-van Oorschot (1997), with plasmid pMT2SM-AAP-5 encoding the myc-tagged AAP-5 protein, respectively. By indirect immunofluorescence using the myc-tag-specific antibody 9E10 and DAPI, which stains the nuclear DNA, it was shown that AAP-5 protein was present both in the nucleus as well as in the cytoplasm of most of the tumor cells and in a minor part of the cells in the nucleus or cytoplasm alone. In cells in which both the nucleus and cytoplasm were stained with AAP-5, the nuclear staining was somewhat more positive. Co-expression of AAP-5 and Apoptin resulted in a more concrete 'thready/blobby' structural entities containing both AAP-5 and Apoptin. These structures are present mainly in the cytoplasm but alsowithin the nucleus. These observations illustrate that AAP-5 and Apoptin clearly can co-localize with each other.

Already, three days after transfection, a significant amount of Saos-2 cells and U2OS cells synthesizing AAP-5 underwent induction of apoptosis. These AAP-5-positive cells were aberrantly stained with DAPI, which is indicative for induction of apoptosis (Telford, 1992, Danen-van Oorschot, 1997). Four days after transfection, the level of apoptotic AAP-5-positive cells even increased. Cells expressing Apoptin also underwent apoptosis, whereas as expected the cells synthesizing the non-apoptotic beta-galactosidase (LacZ) protein did not. Co-expression of both Apoptin and AAP-5 proteins in human tumor cells, such as Saos-2 cells, results in a slightly faster apoptotic process as expression of Apoptin or AAP-5 protein alone. The results are shown in Table 1.

TABLE 1

Apoptosis activity in human tumor Saos-2 cells induced by AAP-5, alone or in combination with Apoptin

| Days after transfection | Synthesized Proteins | | | |
|---|---|---|---|---|
| | LacZ | AAP-5 | Apoptin | AAP-5/Apoptin |
| 3 days | – | + | + | ++ |
| 4 days | – | ++ | + | +++ |

Table 1 shows the apoptotic activity of AAP-5 protein, with or without co-synthesis of Apoptin in human osteosarcoma-derived Saos-2 cells. As positive control, Saos-2 cells were transfected with a plasmid encoding Apoptin. As negative control, cells were transfected with a plasmid encoding lacZ. Note: (–): no apoptotic activity; (+): apoptotic activity; (++): strong apoptotic activity; (+++): very strong apoptotic activity. Three independent experiments were carried out.

The fact that AAP-5 protein can induce apoptosis in p53-minus Saos-2 cells indicates that AAP-5 can induce p53-independent apoptosis. These results imply that AAP-5 can be used as antitumor agent in cases where other (chemo) therapeutic agents will fail. Furthermore, the finding that both Apoptin and AAP-5 induce a p53-independent pathway indicates that AAP-5 fits in the Apoptin-induced apoptotic pathway.

In conclusion, we have identified an Apoptin-associating protein, namely the novel AAP-5 protein, which is mainly present in the nucleus and able to induce (p53-independent) apoptosis in human tumor cells.

The putative BRCA-binding protein BRIP1 also shows some amino-acid sequence homologies with AAP-5. Sequence homology analysis of AAP-5 with known DNA and amino-acid sequences revealed some homology (Table 2) with the human putative BRCA-binding protein BRIP1. The cellular BRCA protein is related with tumor formation. The fact that the Apoptin-associating protein AAP-5 shows some homology with a putative BRCA-binding protein, suggests that AAP-5 also is tumor-related, which is in agreement with the finding that AAP-5 is part of the tumor-specific pathway of Apoptin-induced apoptosis.

TABLE 2

| AAP-5 | PMAEFMDYTS (SEQ ID NO 24) | SQCGKYYSSV (SEQ ID NO 25) | PEEGGATHVY (SEQ ID NO 26) |
|---|---|---|---|
| *BRIP1 | ------------------ | -----------GTSSC (SEQ ID NO 27) | RRVRACGRIH (SEQ ID NO 28) |
| consensus | | SS | A   IH |

TABLE 2-continued

| AAP-5 | RYHRGESKLH (SEQ ID NO 29) | MCLDIGNGQR (SEQ ID NO 30) | KDRKKTSLGP (SEQ ID NO 31) |
|---|---|---|---|
| BRIP1 | HNMANLFIRK (SEQ ID NO 32) | MVNPLLYLSR (SEQ ID NO 33) | HTVKPRALST (SEQ ID NO 34) |
| consensus | M       I       R | K       AL | |
| AAP-5 | GGSYQISEHA (SEQ ID NO 35) | PEASQPAENI (SEQ ID NO 36) | SKDLYIEVYP (SEQ ID NO 37) |
| BRIP1 | FLFGSIRSAA (SEQ ID NO 38) | PVAVEPGAAV (SEQ ID NO 39) | RSLLSPGLLP (SEQ ID NO 40) |
| consensus | I   A | P   A   PA   I | L       LP |
| AAP-5 | GTYSVTVGSN (SEQ ID NO 41) | DLTKKTHVVA (SEQ ID NO 42) | VDSGQSVDLV (SEQ ID NO 43) |
| BRIP1 | HLLPALGFKN (SEQ ID NO 44) | KTVLKKRCKD (SEQ ID NO 45) | CYLVKRRGRW (SEQ ID NO 46) |
| consensus | N | K | |
| AAP-5 | FPV | | |
| BRIP1 | YVY | | |
| consensus | F | | |

*BRIP1 protein sequence derived from AAF04788, which is derived from BRIP1 DNA sequence AF151109

Table 2 shows the partial consensus amino-acid sequences of AAP-5 and the putative BRCA-binding protein BRIP-1.

Utility of AAP-5 Antisera

The AAP-5 antibody of the two generated with the highest affinity was selected for further use. The efficacy of this antibody was tested by transfecting primate COS-7 and human U2OS cells with the partial AAP-5-myc construct.

With AAP-5-myc DNA transfections, Western analysis showed that approximately 17 or 12 kD (COS and U2OS, respectively) AAP-5-myc protein was detected strongly, only in samples where the DNA was transfected. (These size differences may be a result of cell-type-specific post-translational modifications.) Similarly, in immunoprecipitation experiments, AAP-5-myc was also strongly detected. Finally, we could detect the presence of transfected AAP-5-myc diffusely in the cytoplasm and nucleus of human Saos-2 tumor cells using the AAP-5 antibody in immunofluorescence analysis.

Northern Blot Analysis

Whereas AAP-5 is not detectably expressed in the fetal tissue RNA examined, there is an approximately 1.8–2 kb message expressed in adult lung. This mRNA size is consistent with what is predicted to be expressed from the full-length gene, including post-transcriptional modifications.

Biochemical Interactions of AAP-5 with other Apoptin-associating Proteins

The genetic yeast screen with pGBT-VP3 as bait plasmid and pACT plasmid containing CDNAs from transformed human B cells also delivered other Apoptin-associating proteins, which also encode Apoptin-associating proteins. These Apoptin-associating proteins were called AAP-3 and AAP-4 (see co-pending application EP01200163.2 and EP00204396.6 respectively, which are incorporated herein by reference). The DNA sequence of AAP-3 is shown in SEQ ID NO 20. SEQ ID NO 20 shows the partial sequence of vector pMT2SM-AAP-3.

```
CCGATGGTAG  GCGGCGGCGG  GGTCGGCGGC  GGCCTCCTGG  AGAATGCCAA
CCCCCTCATC  TACCAGCGCT  CTGGGGAGCG  GCCTGTGACG  GCAGGCGAGG
AGGACGAGCA  GGTTCCCGAC  AGCATCGACG  CACGCGAGAT  CTTCGARCTG
ATTCGCTCCA  TCAATGACCC  GGAGCATCCA  CTGACGCTAG  AGGAGTTGAA
CGTAGTAGAG  CAGGTGCGGG  TTCAGGTTAG  CGACCCCGAG  AGTACAGTGG
CTGTGGCTTT  CACACCAACC  ATTCCGCACT  GCAGCATGGC  CACCCTTATT
GGTCTGTCCA  TCAAGGTCAA  GCTTCTGCGC  TCCCTTCCTC  AGCGTTTCAA
GATGGACGTG  CACATTACTC  CGGGGACCCA  TGCCTCAGAG  CATGCAGTGA
ACAAGCAACT  TGCAGATAAG  GAGCGGGTGG  CAGCTGCCCT  GGAGAACACC
CACCTCTTGG  AGGTTGTGAA  TCAGTGCCTG  TCAGCCCGCT  CCTGAGCCTG
GCCTTTGACC  CCTCAACCTG  CATACTGGGT  ATCCTGGTCC  CAACTCCTGC
CAAGGGCTGT  TACCGTTGTT  TTCCTGGAAT  CACTCACAAA  TGAGAAACTA
ACATTTGCCT  TTTTGTAATA  AAGTTAATTT  ATATTCAAAA  AAAAAAAAAA
C (SEQ ID NO 20)
```

The AAP-3 CDNA-encoded amino acid sequence is shown in SEQ ID NO 21. HEGPMVGGGGVGGGLLENA-NPLIYQRSGERPVTAGEEDEQVPDSIDA-REIFDLIRSINDP EHPLTLEELNVVEQVRVQVSD-PESTVAVAFTPTIPHCSMATLIGLSIKVKLLRSLPQR FKM DVHITPGTHASEHAVNKQLADKER-VAAALENTHLLEVVNQCLSARS (SEQ ID NO 21). SEQ ID NO 21 shows the amino acid sequence of the analyzed region of the Apoptin-associating clone AAP-3. In addition to, the three C-terminal amino acids H-E-G (bold) of the multiple cloning site of pact are given to illustrate that the AAP-3 amino acid sequence is in frame with the GAL4-activation domain. This feature proves that the AAP-3 region is indeed synthesized in yeast cells.

The DNA sequence of the AAP-4 CDNA starts at position 12 of the DNA sequence and is indicated as "start AAP-4 CDNA". This feature proves that the AAP-4 region is indeed synthesized in yeast cells. The DNA sequence of AAP-4 is shown in SEQ ID NO 22. GCCACGAAGGCCGG-GAGAGCTCGCCCTGCACCTACAT-AACTCGGCGGTCAGTGAGG ACAAGAACAAATCT-GAAGGAGGCCTCTGACATCAAGCTTGAACCAAA TACGTTGAA TGGCTATAAAAGCAGTGTGACG-GAACCTTGCCCCGACAGTGGTGAACAGCTGCAGC CAGCTCCTGTGCTGCAGGAGGAA-GAACTGGCTCATGAGACTGCACAAAAAGGGGAG GCAAAGTGTCATAAGAGTGACACAG-GCATGTCCAAAAAGAAGTCACGACAAGGAAAACT-TGTGAAACAGTTTGCAAAAATAGAG-GAATCTACTCCAGTGCACGATTCTCCTGG AAAAGACGACGCGGTACCA-GATTTGATGGGTCCCCATTCTGAC-CAGGGTGAGCACA GTGGCACTGTGGGCGTGCCT-GTGAGCTACACAGACTGTGCTCCTTCACCCGTC GGTT GTTCAGTTGTGACATCAGATAGCT-TCAAAACAAAAGACAGCTTTAGAACTGCAAAA AAGTAAAAAGAAGAGGCGAATCACAAGG-TATGATGCACAGTTAATCCTAGAAAATA ACTCTGG-GAGTCCCAAATTGACTCTTCGTAGGCGT-CATGATAGCAGCAGCAAAACA AATGGACCAAGAGAATGATGGGAAT-GAAACTCTTCCCAAAATTAAGCATCAAGTTTAAGC-CAAAGACCATGACAACGATAACAATCTC-GATGTAGCAAAGTTATAAGGCTTT AGCTCAGGATTAGGAATGTTTCA-CAAAATTAAAAAGGCAT (SEQ ID NO 22). SEQ ID NO 22 shows the partial sequence of vector pMT2SM-AAP-4. The DNA sequence of the AAP-4 CDNA starts at position 12 of the DNA sequence and is indicated as "start AAP-4 CDNA".

The AAP-4 CDNA-encoded amino acid sequence is shown in SEQ ID NO 23. HEGRESSPCTYITRRSVRTRT-NLKEASDIKLEPNTLNGYKSSVTEPCP-DSGEQLQPAPVLQ EEELAHETAQKGEAKCHKSDT-GMSKKKSRQGKLVKQFAKIEESTPVHDSPGKDDA VPDL MGPHSDQGEHSGTVGVPVSYTD-CAPSPVGCSVVTSDSFKTKDSFRTAKKX-KEEANHKVXC TVNPRKXLWESQIDSSXASXX-QQQNKWTKRMMGMKLFPKLSIKFKPKTMTTITIS MXQSY KGLAQDXECFTKLKRH (SEQ ID NO 23). Just like AAP-5, both AAP-3 and AAP-4 are able to associate with Apoptin not only in the yeast background, but also in a mammalian transformed cellular system. SEQ ID NO 23 shows the amino acid sequence of the analyzed region of the Apoptin-associating clone AAP-4. In addition to, the three C-terminal amino acids H-E-G (bold) of the multiple cloning site of pact are given to illustrate that the AAP-4 amino acid sequence is in frame with the GAL4-activation domain.

Immunofluorescence assays of human transformed Saos-2 cells and normal diploid VH10 fibroblasts expressing AAP-3 revealed that AAP-3 is located in both cell types predominantly in the cytoplasm and nucleus, but in lower percentages also mainly in the nucleus or mainly in the cytoplasm. Co-synthesis of AAP-3 and Apoptin in both cell types showed a clear nuclear localization of AAP-3 and Apoptin. Tumor cells that have become apoptotic showed a nuclear localization of Apoptin and a peri-nuclear staining pattern of AAP-3. As expected, normal diploid VH10 cells synthesizing both Apoptin and AAP-3 did not undergo apoptosis.

AAP-4 is present in the nucleus and able to induce (p53-independent) apoptosis in human tumor cells. To study whether other Apoptin-associating proteins can also bind to AAP-5 multiple experiments were performed. First, we tested the ability of AAP-5 to bind to AAP-3 in co-IP analysis, and found that these two proteins do interact under these conditions. However, we showed that AAP-5 does not bind to AAP-4 (even though AAP-3 does bind to AAP-4) under these conditions. These results show that many Apoptin-associating proteins can exist in heterocomplexes.

Cloning and Sequence Analysis of Full-length AAP-5

A further sequence analysis of the human AAP-5 sequence yielded the 974 bp long nucleic acid sequence as shown in SEQ ID NO 9. SEQ ID NO 9 specifically shows the nucleic acid sequence of full-length AAP-5.

```
CTGCGCCGGC  GCCGCCGGGA  GCGCTAGGCC  TGGTCCCTCT  TCCTAGGATA
GCGTTGCGCG  CATGCGCCTT  GACGAGTGAG  CCGGGGAGCC  ATGGACAACT
GTTTGGCGGC  CGCAGCGCTG  AATGGGGTGG  ACCGACGTTC  CCTGCAGCGT
TCAGCAAAGC  TGGCTCTAGA  AGTGCTGGAG  AGGGCCAAGA  GGAGGGCGGT
GGACTGGCAT  GCCCTGGAGC  GTCCCAAAGG  CTGCATGGGG  GTCCTTGCCC
GGGAGGCGCC  CCACCTAGAG  AAACAGCCGG  CAGCCGGCCC  GCAGCGCGTT
CTCCCGGGAG  AGAGAGAAGA  GAGACCCCCA  ACCCTTAGTG  CTTCCTTCAG
AACAATGGCT  GAATTCATGG  ACTATACTTC  AAGTCAGTGT  GGGAAATATT
ATTCATCTGT  GCCAGAGGAA  GGAGGGGCAA  CCCATGTCTA  TCGTTATCAC
AGAGGCGAGT  CGAAGCTGCA  CATGTGCTTG  GACATAGGGA  ATGGTCAGAG
AAAAGACAGA  AAAAAGACAT  CCCTTGGTCC  TGGAGGCAGC  TATCAAATAT
CAGAGCATGC  TCCAGAGGCA  TCCCAGCCTG  CTGAGAACAT  CTCTAAGGAC
CTCTACATAG  AAGTATATCC  AGGGACCTAT  TCTGTCACTG  TGGGCTCAAA
TGACTTAACC  AAGAAGACTC  ATGTGGTAGC  AGTTGATTCT  GGACAAAGCG
TGGACCTGGT  CTTCCCTGTG  TGATGTTGAC  CATCACTGCC  ATCACATCAC
CTTTTTTTAA  GTAGTAAGAA  TAAAGCCACT  GTATGATTCT  CTTAATAGCT
ATACATTAAT  CCTGTTTTTA  GTGCTGACTG  GGTCAGCCTT  CCGGGAACTG
GAGTCTGTCT  CTTTCAGTGC  TTTTTTGTTT  GTTTGGTTGG  TTTTTTTTTG
AGACAGTCTC  ACTCTGTTGC  CCAGGCTGGA  GTGCAGTGGC  GTGATCTCGG
CTCACTGCAA  GTTCCGCCTC  CCGG        (SEQ ID NO 9)
```

The ATG start codon is at position 91–93 and the TAA stop codon is at position 793–795. An open reading frame was found in this nucleic acid sequence at position 91 to 795. The deduced amino acid sequence is given in SEQ ID NO 10. MDNCLAAAALNGVDRRSLQRSAKLALEV-LERAKRRAVDWHALERPKGCMGVLAREA PHLEKQ-PAAGPQRVLPGEREERPPTLSASFRT-MAEFMDYTSSQCGKYYSSVPEEGGATH VYRYHRGESKLHM-CLDIGNGQRKDRKKTSLGPGGSYQISE-HAPEASQPAENISKDLYIE VYPGTYSVTVGSNDLT-KKTHVVAVDSGQSVDLVFPV (SEQ ID NO 10). SEQ ID NO 10 shows the amino acid sequence deduced from the nucleic acid sequence of SEQ ID NO 9.

AAP-5: Appearance and Effects on Tumor Cells

Full-length AAP-5 in both Saos-2 and U2OS cells exhibited a primarily cytoplasmic localization. The staining was diffuse, but in addition most of the cells also contained very prominent bodies in the cytoplasm, clustering in particular around the nucleus. These bodies had a semi-regular, almost crystalline structure, and tended to cluster together into larger aggregates. In some cells a faint nuclear, diffuse staining could also be discerned. When co-expressed with Apoptin, it appeared that Apoptin formed a "shell" around the outside of the crystalline-like bodies, and the overall number of these bodies appeared to be decreased compared to the situation with the AAP-5 expressed alone.

We also examined the apoptosis potential of the full-length AAP-5 in both Saos-2 and U2OS cells. Compared to the lacZ negative control, AAP-5 caused a very high percentage of apoptosis in both cell types, almost twice the level as that seen for Apoptin alone at the same time point (2 days after transfection). This apoptosis only increased at later time points, similar to what was seen with the partial AAP-5 protein. Also similar to the partial AAP-5 protein, when co-expressed with Apoptin, there was a slight increase in the amount of death as compared to either protein expressed alone.

The apoptosis inducing capability of the partial AAP-5 protein or the full-length AAP-5 protein alone or in combination with Apoptin shows that all possible mutants ranging from at least the partial AAP-5 protein to the full-length AAP-5 protein are capable of inducing apoptosis. Therefore, deletion mutants of the full-length AAP-5 protein comprising at least the partial AAP-5 protein are capable of inducing apoptosis. Also, point mutants (both at nucleotide and amino acid level) of the full-length AAP-5 protein comprising at least the partial AAP-5 protein are capable of inducing apoptosis.

Expression and Detection of Full-length AAP-5 on Western Blot

Finally, western analysis of the full-length AAP-5 protein expressed in COS-cells followed by ECL analysis using the anti-myc tag antibody 9E10. showed a specific band consistent with the predicted size (30 kDa) of the full-length AAP-5.

References

1. Bellamy, C. O. C., Malcomson, R. D. G., Harrison, D. J., and Wyllie, H. 1995. Cell death and disease: The biology and regulation of apoptosis. *Seminars in Cancer biology* 6, 3–12.

2. Danen-Van Oorschot, A. A. A. M., Fischer, D. F., Grimbergen, J. M., Klein, B., Zhuang, S.-M., Falkenburg, J. H. F., Backendorf, C., Quax, P. H. A., Van der Eb, J. A., and Noteborn, M. H. M. (1997). Apoptin induces apoptosis in human transformed and malignant cells but not in normal cells. *Proceedings National Academy Sciences*, USA: 94, 5843–5847.

3. Danen-Van Oorschot, A. A. A. M, Den Hollander, A., Takayama, S., Reed, J., Van der Eb, A. J. and Noteborn, M. H. M. (1997a). BAG-1 inhibits p53-induced but not Apoptin-induced apoptosis. *Apoptosis* 2, 395–402.

4. Duke, R. C., Ocjius, D. M., Young, J, D-E. (1996). Cell suicide in health and disease. *Scientific American December* 1996, 48–55.

5. Durfee, T., Becherer, K., Chen, P.-L., Yeh, S.-H., Yang, Y., Kilburn, A. E., Lee, W.-H., and Elledge, S. J. (1993). The retinoblastoma protein associates with the protein phosphate type I catalytic subunit. *Genes and Development* 7, 555–569.

6. Earnshaw, W. C., 1995. Nuclear changes in apoptosis. *Current Opinion in Cell Biology* 7, 337–343.

7. Fields, S. and Song, O. K. (1989). A novel genetic system to detect protein-protein interactions. *Nature* 340, 245–246.

8. Hockenberry, D. M. (1994). Bcl-2 in cancer, development and apoptosis. *Journal of Cell Science*, Supplement 18, 51–55.

9. Hoffman, C. S. and Winston, F. (1987). A ten-minute DNA preparation from yeast efficiently releases autonomous plasmids for transformation of *Escherichia coli. Gene* 57, 267–272.

10. Kerr, J. F. R., Winterford, C. M., and Harmon, B. V. (1994). Apoptosis: Its significance in cancer and cancer therapy. *Cancer* 73, 2013–2026.

11. Klebe, R. J., Harriss, J. V., Sharp, Z. D., and Douglas, M. G. (1983). A general method for polyethylene-glycol-induced genetic transformation of bacteria and yeast. *Gene* 25, 333–341.

12. Levine, A. J. (1997). p53, the cellular gatekeeper for growth and division. *Cell* 88, 323–331.

13. Maniatis, T., Fritsch, E. F., and Sambrook, J. (1982). Molecular Cloning: A Laboratory Manual. CSHL Press, New York, USA.

14. McDonell T. J., Meyn, R. E., Robertson, L. E. (1995). Implications of apoptotic cell death regulation in cancer therapy. *Seminars in Cancer Biology* 6, 53–60.

15. Noteborn, M. H. M. (1996). PCT application WO 96/41191. Apoptin induces apoptosis in human transformed and malignant cells but not in normal cells as essential characteristic for the development of an anti-tumor therapy.

16. Noteborn, M. H. M., and De Boer, G. F. (1996). U.S. patent application Ser. No. 09/030,335.

17. Noteborn, M. H. M., De Boer, G. F., Van Roozelaar, D., Karreman, C., Kranenburg, O., Vos, J., Jeurissen, S., Zantema, A., Hoeben, R., Koch, G., Van Ormondt, H., and Van der Eb, A. J. (1991). Characterization of cloned chicken anemia virus DNA that contains all elements for the infectious replication cycle. *Journal of Virology* 65, 3131–3139.

18. Noteborn, M. H. M., and Pietersen, A. (1998). A gene delivery vehicle expressing the apoptosis-inducing proteins VP2 and/or Apoptin. PCT Application PCT/NL98/00213

19. Noteborn, M. H. M., Todd, D., Verschueren, C. A. J., De Gauw, H. W. F. M., Curran, W. L., Veldkamp, S., Douglas, A. J., McNulty, M. S., Van der Eb, A. J., and Koch, G. (1994). A single chicken anemia virus protein induces apoptosis. *Journal of Virology* 68, 346–351.

20. Noteborn, M. H. M., Verschueren, C. A. J., Koch, G., and Van der Eb, A. J. (1998). Simultaneous expression of recombinant baculovirus-encoded chicken anemia virus (CAV) proteins VP1 and VP2 is required for formation of the CAV-specific neutralizing epitope. *Journal General Virology,* 79, 3073–3077.

21. Noteborn, M. H. M., and Zhang, Y. (1998). Methods and means for determining the transforming capability of agents, for determining the predisposition of cells to become transformed and prophylactic treatment of cancer using Apoptin-like activity. PCT Application PCT/NL98/00457

22. Noteborn, M. H. M., Danen-van Oorschot, A. A. A. M., Van der Eb, A. J. (1998a). Chicken anemia virus: Induction of apoptosis by a single protein of a single-stranded DNA virus. *Seminars in Virology* 8, 497–504.

23. Paulovich, A. G., Toczyski, D., Hartwell, H. (1997). When checkpoints fail. *Cell* 88, 315–321.

24 Pietersen, A. M., Van der Eb, M. M., Rademaker, H. J., Van den Wollenberg, D. J. M., Rabelink, M. J. W. E., Kuppen, P. J. K., Van Dierendonck, J. H., Van Ormondt, H., Masman, D., Van de Velde, C. J. H., Van der Eb, Hoeben, R. C., and Noteborn, M. H. M. (1998). Specific tumor-cell killing with adenovirus vectors containing the Apoptin gene. *Gene Therapy* 6, 882–892.

25. Rose, M. D., Winston, F., and Hieter, P. (1990). Methods in yeast genetics. A laboratory course manual. Cold Spring Harbor Laboratory Press, Cold Spring Harbor, N.Y., USA.

26. Sachs, L. and Lotem, J. (1993). Control of programmed cell death in normal and leukemia cells: New implications for therapy. *Blood* 82, 15–21.

27. Sanger, F., Nicklen, S., and Coulsen, A. R. (1977). DNA sequencing with chain-terminating inhibitors. *Proceedings National Academic Sciences USA* 74, 5463–5467.

28. Steller, H. (1995). Mechanisms and genes of cellular suicide. *Science* 267, 1445–1449.

29. Telford, W. G., King, L. E., Fraker, P. J. (1992). Comparative evaluation of several DNA binding dyes in the detection of apoptosis-associated chromatin degradation by flow cytometry. *Cytometry* 13, 137–143.

30. Teodoro, J. G. and Branton, P. E. (1997). Regulation of apoptosis by viral gene products. *Journal of Virology* 71, 1739–1746.

31. Thompson, C. B. (1995). Apoptosis in the pathogenesis and treatment of disease. *Science* 267, 1456–1462.

32. White, E. (1996). Life, death, and the pursuit of apoptosis. *Genes and development* 10, 1–15.

33. Wyllie, A. H. (1995). The genetic regulation of apoptosis. *Current Opinion in Genetics and Development* 5, 97–104.

34. Wyllie, A. H., Kerr, J. F. R., Currie, A. R. (1980). Cell death: The significance of apoptosis. *International Review of Cytology* 68, 251–306.

35. Yang, X., Hubbard, E. J. A., and Carlson, M. (1992). A proteinkinase substrate identified by the two-hybrid system. *Science* 257, 680–682.

36. Zhuang, S.-M., Landegent, J. E., Verschueren, C. A. J., Falkenburg, J. H. F., Van Ormondt, H., Van der Eb, A. J., Noteborn, M. H. M. (1995). Apoptin, a protein encoded by chicken anemia virus, induces cell death in various human hematologic malignant cells in vitro. *Leukemia* 9 S1, 118–120.

37. Zhuang, S.-M., Shvarts, A., Van Ormondt, H., Jochemsen, A.-G., Van der Eb, A. J., Noteborn, M. H. M. (1995). Apoptin, a protein derived from chicken anemia virus, induces a p53-independent apoptosis in human osteosarcoma cells. *Cancer Research* 55, 486–489.

38. Noteborn et. al. (2000) European patent application 01200163.2, Apoptin-associating protein 39. Noteborn et al. (2000) European patent application 00204396.6, Apoptin-associating protein 40. Evans G I, Lewis G K, Ramsay G, Bishop J M (1985), Isolation of monoclonal antibodies specific for human c-myc proto-oncogene product. *Mol Cell Biol.* Dec 5(12), 3610–3616.

What is claimed is:

1. A method of inducing apoptosis in a cell comprising administering to said cell an apoptosis inducing substance selected from the group consisting of:
   an isolated nucleic acid of SEQ ID NO 1 or SEQ ID NO 9,
   a vector comprising an isolated nucleic acid of SEQ ID NO 1 or SEQ ID NO 9, and
   mixtures thereof,
   wherein said isolated nucleic acid is operatively linked to an element capable of expressing a protein encoded by said isolated nucleic acid.

2. The method according to claim 1 wherein said apoptosis inducing substance is administered to a p53-minus cell.

3. A method for treating a subject having a disease wherein enhanced cell proliferation or decreased cell death is observed, said method comprising:
   providing a cell having enhanced proliferation or decreased cell death with a pharmaceutically acceptable amount of a component selected from the group consisting of:
   an isolated nucleic acid of SEQ ID NO 1 or SEQ ID NO 9,
   a vector comprising an isolated nucleic acid of SEQ ID NO 1 or SEQ ID NO 9, and
   mixtures thereof,
   wherein said isolated nucleic acid is operatively linked to an element capable of expressing a protein encoded by said isolated or recombinant nucleic acid.

4. The method according to claim 3 wherein said disease comprises cancer or auto-immune disease.

5. The method according to claim 3 wherein said apoptosis inducing substance is administered to a p53-minus cell.

* * * * *

SEQUENCE LISTING

<160> NUMBER OF SEQ ID NOS: 46

<210> SEQ ID NO 1
<211> LENGTH: 981
<212> TYPE: DNA
<213> ORGANISM: vector pMT2SM-AAP-5

<400> SEQUENCE: 1

| | | |
|---|---|---|
| ccaatggctg aattcatgga ctatacttca agtcagtgtg ggaaatatta ttcatctgtg | 60 |
| ccagaggaag gagggggcaac ccatgtctat cgttatcaca gaggcgagtc gaagctgcag | 120 |
| atgtgcttgg acatagggaa tggtcagaga aagacagaa aaaagacatc ccttggtcct | 180 |
| ggaggcagct atcaaatatc agagcatgct ccagaggcat cccagcctgc tgagaacatc | 240 |
| tctaaggacc tctacataga agtatatcca gggacctatt ctgtcactgt gggctcaaat | 300 |
| gacttaacca agaagactca tgtggtagca gttgattctg gacaaagcgt ggacctggtc | 360 |
| ttccctgtgt gatgttgacc atcactgcca tcacatcacc ttttttttaag tagtaagaat | 420 |
| aaagccactg tatgattctc ttaatagcta tacattaatc ctgttttttag tgctgactgg | 480 |
| gtcagccttc cgggaactgg agtctgtctc tttcagtgct tttttgtttg tttggttggt | 540 |
| tgtttttttga gacagtctcg ctctgttgcc caggctggag tgcagtggcg tgatctcggc | 600 |
| tcaccgcaag ttccgcctcc cgggttcaca ccattctcct gcctcagcct cccgagtagc | 660 |
| tggcactaca ggcacccgcc accatgcccg gctattttt ttgtattttt agtagagacg | 720 |
| gggtttcacc atgttggcca ggatggtctc gatctcttga cctcgtgatc cacccacctt | 780 |
| ggcctcccaa agtgttggga ttacaggcgt gagccaccgc gcccggcctc agtgccttt | 840 |
| ttaacttgag ggtgtagagg tcctccacgc ttgtttgcct gaaagtaata taatgatgct | 900 |
| gtctgaacag gttttactgc ttgctttcca agtaaaggtt aattatgata ataaagagat | 960 |
| ttgggccttc gtggcctcga g | 981 |

<210> SEQ ID NO 2
<211> LENGTH: 126
<212> TYPE: PRT
<213> ORGANISM: vector pMT2SM-AAP-5

<400> SEQUENCE: 2

His Glu Gly Pro Met Ala Glu Phe Met Asp Tyr Thr Ser Ser Gln Cys
1               5                   10                  15

Gly Lys Tyr Tyr Ser Ser Val Pro Glu Glu Gly Gly Ala Thr His Val
            20                  25                  30

Tyr Arg Tyr His Arg Gly Glu Ser Lys Leu His Met Cys Leu Asp Ile
        35                  40                  45

Gly Asn Gly Gln Arg Lys Asp Arg Lys Lys Thr Ser Leu Gly Pro Gly
    50                  55                  60

Gly Ser Tyr Gln Ile Ser Glu His Ala Pro Glu Ala Ser Gln Pro Ala
65                  70                  75                  80

Glu Asn Ile Ser Lys Asp Leu Tyr Ile Glu Val Tyr Pro Gly Thr Tyr
                85                  90                  95

Ser Val Thr Val Gly Ser Asn Asp Leu Thr Lys Lys Thr His Val Val
            100                 105                 110

Ala Val Asp Ser Gly Gln Ser Val Asp Leu Val Phe Pro Val
        115                 120                 125

<210> SEQ ID NO 3
<211> LENGTH: 17
<212> TYPE: DNA
<213> ORGANISM: pACT-specific primer

<400> SEQUENCE: 3
taccactaca atggatg                                                    17

<210> SEQ ID NO 4
<211> LENGTH: 16
<212> TYPE: PRT
<213> ORGANISM: partial AAP-5 clone peptide

<400> SEQUENCE: 4

Cys Gly Gly Ala Thr His Val Tyr Arg Tyr His Arg Gly Glu Ser Lys
1               5                   10                  15

<210> SEQ ID NO 5
<211> LENGTH: 16
<212> TYPE: PRT
<213> ORGANISM: partial AAP-5 clone peptide

<400> SEQUENCE: 5

Gly Asn Gly Gln Arg Lys Asp Arg Lys Lys Thr Ser Leu Gly Pro Cys
1               5                   10                  15

<210> SEQ ID NO 6
<211> LENGTH: 16
<212> TYPE: PRT
<213> ORGANISM: partial AAP-5 clone peptide

<400> SEQUENCE: 6

Glu His Ala Pro Glu Ala Ser Gln Pro Ala Glu Asn Ile Ser Lys Cys
1               5                   10                  15

<210> SEQ ID NO 7
<211> LENGTH: 28
<212> TYPE: DNA
<213> ORGANISM: AAP-5  5'primer

<400> SEQUENCE: 7
ggagccatgg acaactgttt ggcggccg                                        28

<210> SEQ ID NO 8
<211> LENGTH: 28
<212> TYPE: DNA
<213> ORGANISM: AAP-5  3'primer

<400> SEQUENCE: 8
gtgatggcag tgatggtcaa catcacac                                        28

<210> SEQ ID NO 9
<211> LENGTH: 974
<212> TYPE: DNA
<213> ORGANISM: AAP-5

<400> SEQUENCE: 9
ctgcgccggc gccgccggga gcgctaggcc tggtccctct tcctaggata gcgttgcgcg      60
catgcgcctt gacgagtgag ccggggagcc atgacaact gttggcggc cgcacgcgctg     120 aatggggtgg accgacgttc cctgcagcgt tcagcaaagc tggctctaga agtgctggag     180
agggccaaga ggaggcggt ggactggcat gccctggagc gtcccaaagg ctgcatgggg     240
gtccttgccc gggaggcgcc ccacctagag aaacagccgg cagccggccc gcagcgcgtt     300

-continued

```
ctcccgggag agagagaaga gagaccccca acccttagtg cttccttcag aacaatggct    360
gaattcatgg actatacttc aagtcagtgt gggaaatatt attcatctgt gccagaggaa    420 ggagggcaa cccatgtcta tcgttatcac agaggcgagt cgaagctgca catgtgcttg     480
gacataggga atggtcagag aaaagacaga aaaaagacat cccttggtcc tggaggcagc    540
tatcaaatat cagagcatgc tccagaggca tcccagcctg ctgagaacat ctctaaggac    600
ctctacatag aagtatatcc agggacctat tctgtcactg tgggctcaaa tgacttaacc    660
aagaagactc atgtggtagc agttgattct ggacaaagcg tggacctggt cttccctgtg    720
tgatgttgac catcactgcc atcacatcac cttttttttaa gtagtaagaa taaagccact    780
gtatgattct cttaatagct atacattaat cctgttttta gtgctgactg ggtcagcctt    840
ccgggaactg gagtctgtct ctttcagtgc ttttttgttt gtttggttgg tttttttttg    900
agacagtctc actctgttgc ccaggctgga gtgcagtggc gtgatctcgg ctcactgcaa    960
gttccgcctc ccgg                                                      974
```

<210> SEQ ID NO 10
<211> LENGTH: 210
<212> TYPE: PRT
<213> ORGANISM: open reading frame of AAP-5

<400> SEQUENCE: 10

```
Met Asp Asn Cys Leu Ala Ala Ala Leu Asn Gly Val Asp Arg Arg
1               5                   10                  15

Ser Leu Gln Arg Ser Ala Lys Leu Ala Leu Glu Val Leu Glu Arg Ala
            20                  25                  30

Lys Arg Arg Ala Val Asp Trp His Ala Leu Glu Arg Pro Lys Gly Cys
        35                  40                  45

Met Gly Val Leu Ala Arg Glu Ala Pro His Leu Glu Lys Gln Pro Ala
    50                  55                  60

Ala Gly Pro Gln Arg Val Leu Pro Gly Glu Arg Glu Arg Pro Pro
65                  70                  75                  80

Thr Leu Ser Ala Ser Phe Arg Thr Met Ala Glu Phe Met Asp Tyr Thr
                85                  90                  95

Ser Ser Gln Cys Gly Lys Tyr Tyr Ser Ser Val Pro Glu Glu Gly Gly
            100                 105                 110

Ala Thr His Val Tyr Arg Tyr His Arg Gly Glu Ser Lys Leu His Met
        115                 120                 125

Cys Leu Asp Ile Gly Asn Gly Gln Arg Lys Asp Arg Lys Lys Thr Ser
    130                 135                 140

Leu Gly Pro Gly Gly Ser Tyr Gln Ile Ser Glu His Ala Pro Glu Ala
145                 150                 155                 160

Ser Gln Pro Ala Glu Asn Ile Ser Lys Asp Leu Tyr Ile Glu Val Tyr
                165                 170                 175

Pro Gly Thr Tyr Ser Val Thr Val Gly Ser Asn Asp Leu Thr Lys Lys
            180                 185                 190

Thr His Val Val Ala Val Asp Ser Gly Gln Ser Val Asp Leu Val Phe
        195                 200                 205

Pro Val
    210
```

<210> SEQ ID NO 11
<211> LENGTH: 23
<212> TYPE: DNA

<213> ORGANISM: AAP-5 - #5F

<400> SEQUENCE: 11
atattattca tctgtgccag agg     23

<210> SEQ ID NO 12
<211> LENGTH: 23
<212> TYPE: DNA
<213> ORGANISM: AAP-5 - #5R

<400> SEQUENCE: 12
cctctggcac agatgaataa tat     23

<210> SEQ ID NO 13
<211> LENGTH: 15
<212> TYPE: PRT
<213> ORGANISM: Peptides used for raising antibodies against AAP-3

<400> SEQUENCE: 13

Ile Tyr Gln Arg Ser Gly Glu Arg Pro Val Thr Ala Gly Glu Glu
1               5                   10                  15

<210> SEQ ID NO 14
<211> LENGTH: 15
<212> TYPE: PRT
<213> ORGANISM: Peptides used for raising antibodies against AAP-3

<400> SEQUENCE: 14

Asp Glu Gln Val Pro Asp Ser Ile Asp Ala Arg Glu Ile Phe Asp
1               5                   10                  15

<210> SEQ ID NO 15
<211> LENGTH: 15
<212> TYPE: PRT
<213> ORGANISM: Peptides used for raising antibodies against AAP-3

<400> SEQUENCE: 15

Arg Ser Ile Asn Asp Pro Glu His Pro Leu Thr Leu Glu Glu Leu
1               5                   10                  15

<210> SEQ ID NO 16
<211> LENGTH: 15
<212> TYPE: PRT
<213> ORGANISM: Peptides used for raising antibodies against AAP-3

<400> SEQUENCE: 16

Glu Glu Ser Thr Pro Val His Asp Ser Pro Gly Lys Asp Asp Ala
1               5                   10                  15

<210> SEQ ID NO 17
<211> LENGTH: 15
<212> TYPE: PRT
<213> ORGANISM: Peptides used for raising antibodies against AAP-3

<400> SEQUENCE: 17

Asp Ser Phe Lys Thr Lys Asp Ser Phe Arg Thr Ala Lys Ser Lys
1               5                   10                  15

<210> SEQ ID NO 18
<211> LENGTH: 15
<212> TYPE: PRT
<213> ORGANISM: Peptides used for raising antibodies against AAP-3

<400> SEQUENCE: 18

Ile Asp Ile Asp Ile Ser Ser Arg Arg Arg Glu Asp Gln Ser Leu
1               5                   10                  15

<210> SEQ ID NO 19
<211> LENGTH: 10
<212> TYPE: PRT
<213> ORGANISM: pMT2SM vector containing a Myc-tag

<400> SEQUENCE: 19

Glu Gln Lys Leu Ile Ser Glu Glu Asp Leu
1               5                   10

<210> SEQ ID NO 20
<211> LENGTH: 651
<212> TYPE: DNA
<213> ORGANISM: partial sequence of vector pMT2SM-AAP-3

<400> SEQUENCE: 20

```
ccgatggtag gcggcggcgg ggtcggcggc ggcctcctgg agaatgccaa ccccctcatc      60
taccagcgct ctggggagcg gcctgtgacg gcaggcgagg aggacgagca ggttcccgac     120
agcatcgacg cacgcgagat cttcgarctg attcgctcca tcaatgaccc ggagcatcca     180
ctgacgctag aggagttgaa cgtagtagag caggtgcggg ttcaggttag cgaccccgag     240
agtacagtgg ctgtggcttt cacaccaacc attccgcact gcagcatggc cacccttatt     300
ggtctgtcca tcaaggtcaa gcttctgcgc tcccttcctc agcgtttcaa gatggacgtg     360
cacattactc cggggaccca tgcctcagag catgcagtga acaagcaact tgcagataag     420
gagcgggtgg cagctgccct ggagaacacc cacctcttgg aggttgtgaa tcagtgcctg     480
tcagcccgct cctgagcctg gcctttgacc cctcaacctg catactgggt atcctggtcc     540
caactcctgc caagggctgt taccgttgtt ttcctggaat cactcacaaa tgagaaacta     600
acatttgcct ttttgtaata aagttaattt atattcaaaa aaaaaaaaaa c              651
```

<210> SEQ ID NO 21
<211> LENGTH: 167
<212> TYPE: PRT
<213> ORGANISM: partial sequence of vector pMT2SM-AAP-3

<400> SEQUENCE: 21

His Glu Gly Pro Met Val Gly Gly Gly Val Gly Gly Gly Leu Leu
1               5                   10                  15

Glu Asn Ala Asn Pro Leu Ile Tyr Gln Arg Ser Gly Glu Arg Pro Val
                20                  25                  30

Thr Ala Gly Glu Glu Asp Glu Gln Val Pro Asp Ser Ile Asp Ala Arg
            35                  40                  45

Glu Ile Phe Asp Leu Ile Arg Ser Ile Asn Asp Pro Glu His Pro Leu
        50                  55                  60

Thr Leu Glu Glu Leu Asn Val Val Glu Gln Val Arg Val Gln Val Ser
65                  70                  75                  80

Asp Pro Glu Ser Thr Val Ala Val Ala Phe Thr Pro Thr Ile Pro His
                85                  90                  95

Cys Ser Met Ala Thr Leu Ile Gly Leu Ser Ile Lys Val Lys Leu Leu
                100                 105                 110

Arg Ser Leu Pro Gln Arg Phe Lys Met Asp Val His Ile Thr Pro Gly
            115                 120                 125

Thr His Ala Ser Glu His Ala Val Asn Lys Gln Leu Ala Asp Lys Glu
        130                 135                 140

```
Arg Val Ala Ala Ala Leu Glu Asn Thr His Leu Leu Glu Val Val Asn
145                 150                 155                 160

Gln Cys Leu Ser Ala Arg Ser
                165
```

<210> SEQ ID NO 22
<211> LENGTH: 770
<212> TYPE: DNA
<213> ORGANISM: AAP-4

<400> SEQUENCE: 22

```
gccacgaagg ccgggagagc tcgccctgca cctacataac tcggcggtca gtgaggacaa      60
gaacaaatct gaaggaggcc tctgacatca agcttgaacc aaatacgttg aatggctata    120
aaagcagtgt gacggaacct tgccccgaca gtggtgaaca gctgcagcca gctcctgtgc    180
tgcaggagga agaactggct catgagactg cacaaaaagg ggaggcaaag tgtcataaga    240
gtgacacagg catgtccaaa agaagtcacg acaaggaaa acttgtgaaa cagtttgcaa    300
aaatagagga atctactcca gtgcacgatt ctcctggaaa agacgacgcg gtaccagatt    360
tgatgggtcc ccattctgac cagggtgagc acagtggcac tgtgggcgtg cctgtgagct    420
acacagactg tgctccttca cccgtcggtt gttcagttgt gacatcagat agcttcaaaa    480
caaaagacag ctttagaact gcaaaaaagt aaaaagaaga ggcgaatcac aaggtatgat    540
gcacagttaa tcctagaaaa taactctggg agtcccaaat tgactcttcg taggcgtcat    600
gatagcagca gcaaaacaaa tggaccaaga gaatgatggg aatgaaactc ttcccaaaat    660
taagcatcaa gtttaagcca agaccatga caacgataac aatctcgatg tagcaaagtt    720
ataaggcttt agctcaggat taggaatgtt tcacaaaatt aaaaaggcat                770
```

<210> SEQ ID NO 23
<211> LENGTH: 256
<212> TYPE: PRT
<213> ORGANISM: AAP-4
<220> FEATURE:
<221> NAME/KEY: misc_feature
<222> LOCATION: (1)..(256)
<223> OTHER INFORMATION: Xaa can be any amino acid

<400> SEQUENCE: 23

```
His Glu Gly Arg Glu Ser Ser Pro Cys Thr Tyr Ile Thr Arg Arg Ser
1               5                   10                  15

Val Arg Thr Arg Thr Asn Leu Lys Glu Ala Ser Asp Ile Lys Leu Glu
            20                  25                  30

Pro Asn Thr Leu Asn Gly Tyr Lys Ser Ser Val Thr Glu Pro Cys Pro
        35                  40                  45

Asp Ser Gly Glu Gln Leu Gln Pro Ala Pro Val Leu Gln Glu Glu Glu
    50                  55                  60

Leu Ala His Glu Thr Ala Gln Lys Gly Glu Ala Lys Cys His Lys Ser
65                  70                  75                  80

Asp Thr Gly Met Ser Lys Lys Ser Arg Gln Gly Lys Leu Val Lys
                85                  90                  95

Gln Phe Ala Lys Ile Glu Glu Ser Thr Pro Val His Asp Ser Pro Gly
                100                 105                 110

Lys Asp Asp Ala Val Pro Asp Leu Met Gly Pro His Ser Asp Gln Gly
            115                 120                 125

Glu His Ser Gly Thr Val Gly Val Pro Val Ser Tyr Thr Asp Cys Ala
        130                 135                 140
```

-continued

```
Pro Ser Pro Val Gly Cys Ser Val Val Thr Ser Asp Ser Phe Lys Thr
145                 150                 155                 160

Lys Asp Ser Phe Arg Thr Ala Lys Lys Xaa Lys Glu Glu Ala Asn His
            165                 170                 175

Lys Val Xaa Cys Thr Val Asn Pro Arg Lys Xaa Leu Trp Glu Ser Gln
        180                 185                 190

Ile Asp Ser Ser Xaa Ala Ser Xaa Xaa Gln Gln Gln Asn Lys Trp Thr
            195                 200                 205

Lys Arg Met Met Gly Met Lys Leu Phe Pro Lys Leu Ser Ile Lys Phe
        210                 215                 220

Lys Pro Lys Thr Met Thr Thr Ile Thr Ile Ser Met Xaa Gln Ser Tyr
225                 230                 235                 240

Lys Gly Leu Ala Gln Asp Xaa Glu Cys Phe Thr Lys Leu Lys Arg His
            245                 250                 255

<210> SEQ ID NO 24
<211> LENGTH: 10
<212> TYPE: PRT
<213> ORGANISM: Sequence homology analysis of AAP-5

<400> SEQUENCE: 24

Pro Met Ala Glu Phe Met Asp Tyr Thr Ser
1               5                   10

<210> SEQ ID NO 25
<211> LENGTH: 10
<212> TYPE: PRT
<213> ORGANISM: Sequence homology analysis of AAP-5

<400> SEQUENCE: 25

Ser Gln Cys Gly Lys Tyr Tyr Ser Ser Val
1               5                   10

<210> SEQ ID NO 26
<211> LENGTH: 10
<212> TYPE: PRT
<213> ORGANISM: Sequence homology analysis of AAP-5

<400> SEQUENCE: 26

Pro Glu Glu Gly Gly Ala Thr His Val Tyr
1               5                   10

<210> SEQ ID NO 27
<211> LENGTH: 5
<212> TYPE: PRT
<213> ORGANISM: Sequence homology analysis of BRIP1

<400> SEQUENCE: 27

Gly Thr Ser Ser Cys
1               5

<210> SEQ ID NO 28
<211> LENGTH: 10
<212> TYPE: PRT
<213> ORGANISM: Sequence homology analysis of BRIP1

<400> SEQUENCE: 28

Arg Arg Val Arg Ala Cys Gly Arg Ile His
1               5                   10

<210> SEQ ID NO 29
<211> LENGTH: 10
```

```
<212> TYPE: PRT
<213> ORGANISM: Sequence homology analysis of AAP-5

<400> SEQUENCE: 29

Arg Tyr His Arg Gly Glu Ser Lys Leu His
1               5                   10

<210> SEQ ID NO 30
<211> LENGTH: 10
<212> TYPE: PRT
<213> ORGANISM: Sequence homology analysis of AAP-5

<400> SEQUENCE: 30

Met Cys Leu Asp Ile Gly Asn Gly Gln Arg
1               5                   10

<210> SEQ ID NO 31
<211> LENGTH: 10
<212> TYPE: PRT
<213> ORGANISM: Sequence homology analysis of AAP-5

<400> SEQUENCE: 31

Lys Asp Arg Lys Lys Thr Ser Leu Gly Pro
1               5                   10

<210> SEQ ID NO 32
<211> LENGTH: 10
<212> TYPE: PRT
<213> ORGANISM: Sequence homology analysis of BRIP1

<400> SEQUENCE: 32

His Asn Met Ala Asn Leu Phe Ile Arg Lys
1               5                   10

<210> SEQ ID NO 33
<211> LENGTH: 10
<212> TYPE: PRT
<213> ORGANISM: Sequence homology analysis of BRIP1

<400> SEQUENCE: 33

Met Val Asn Pro Leu Leu Tyr Leu Ser Arg
1               5                   10

<210> SEQ ID NO 34
<211> LENGTH: 10
<212> TYPE: PRT
<213> ORGANISM: Sequence homology analysis of BRIP1

<400> SEQUENCE: 34

His Thr Val Lys Pro Arg Ala Leu Ser Thr
1               5                   10

<210> SEQ ID NO 35
<211> LENGTH: 10
<212> TYPE: PRT
<213> ORGANISM: Sequence homology analysis of AAP-5

<400> SEQUENCE: 35

Gly Gly Ser Tyr Gln Ile Ser Glu His Ala
1               5                   10

<210> SEQ ID NO 36
<211> LENGTH: 10
<212> TYPE: PRT
<213> ORGANISM: Sequence homology analysis of AAP-5
```

-continued

```
<400> SEQUENCE: 36

Pro Glu Ala Ser Gln Pro Ala Glu Asn Ile
1               5                   10

<210> SEQ ID NO 37
<211> LENGTH: 10
<212> TYPE: PRT
<213> ORGANISM: Sequence homology analysis of AAP-5

<400> SEQUENCE: 37

Ser Lys Asp Leu Tyr Ile Glu Val Tyr Pro
1               5                   10

<210> SEQ ID NO 38
<211> LENGTH: 10
<212> TYPE: PRT
<213> ORGANISM: Sequence homology analysis of BRIP1

<400> SEQUENCE: 38

Phe Leu Phe Gly Ser Ile Arg Ser Ala Ala
1               5                   10

<210> SEQ ID NO 39
<211> LENGTH: 10
<212> TYPE: PRT
<213> ORGANISM: Sequence homology analysis of BRIP1

<400> SEQUENCE: 39

Pro Val Ala Val Glu Pro Gly Ala Ala Val
1               5                   10

<210> SEQ ID NO 40
<211> LENGTH: 10
<212> TYPE: PRT
<213> ORGANISM: Sequence homology analysis of BRIP1

<400> SEQUENCE: 40

Arg Ser Leu Leu Ser Pro Gly Leu Leu Pro
1               5                   10

<210> SEQ ID NO 41
<211> LENGTH: 10
<212> TYPE: PRT
<213> ORGANISM: Sequence homology analysis of AAP-5

<400> SEQUENCE: 41

Gly Thr Tyr Ser Val Thr Val Gly Ser Asn
1               5                   10

<210> SEQ ID NO 42
<211> LENGTH: 10
<212> TYPE: PRT
<213> ORGANISM: Sequence homology analysis of AAP-5

<400> SEQUENCE: 42

Asp Leu Thr Lys Lys Thr His Val Val Ala
1               5                   10

<210> SEQ ID NO 43
<211> LENGTH: 10
<212> TYPE: PRT
<213> ORGANISM: Sequence homology analysis of AAP-5

<400> SEQUENCE: 43
```

```
Val Asp Ser Gly Gln Ser Val Asp Leu Val
1               5                   10

<210> SEQ ID NO 44
<211> LENGTH: 10
<212> TYPE: PRT
<213> ORGANISM: Sequence homology analysis of BRIP1

<400> SEQUENCE: 44

His Leu Leu Pro Ala Leu Gly Phe Lys Asn
1               5                   10

<210> SEQ ID NO 45
<211> LENGTH: 10
<212> TYPE: PRT
<213> ORGANISM: Sequence homology analysis of BRIP1

<400> SEQUENCE: 45

Lys Thr Val Leu Lys Lys Arg Cys Lys Asp
1               5                   10

<210> SEQ ID NO 46
<211> LENGTH: 10
<212> TYPE: PRT
<213> ORGANISM: Sequence homology analysis of BRIP1

<400> SEQUENCE: 46

Cys Tyr Leu Val Lys Arg Gly Arg Trp
1               5                   10
```